United States Patent
De Haan et al.

(10) Patent No.: US 11,299,447 B2
(45) Date of Patent: *Apr. 12, 2022

(54) METHOD FOR ISOLATING A CARBOXYLIC ACID FROM AN AQUEOUS SOLUTION

(71) Applicant: PURAC BIOCHEM BV, Gorinchem (NL)

(72) Inventors: André Banier De Haan, Best (NL);
Jan Van Krieken, Gorinchem (NL);
Tanja Đekic Živkovic,
's-Hertogenbosch (NL)

(73) Assignee: PURAC BIOCHEM B.V., Gorinchem (NL)

( * ) Notice: Subject to any disclaimer, the term of this patent is extended or adjusted under 35 U.S.C. 154(b) by 16 days.

This patent is subject to a terminal disclaimer.

(21) Appl. No.: 14/366,628

(22) PCT Filed: Dec. 21, 2012

(86) PCT No.: PCT/EP2012/076741
§ 371 (c)(1),
(2) Date: Jun. 18, 2014

(87) PCT Pub. No.: WO2013/093047
PCT Pub. Date: Jun. 27, 2013

(65) Prior Publication Data
US 2015/0004663 A1  Jan. 1, 2015

Related U.S. Application Data

(60) Provisional application No. 61/579,730, filed on Dec. 23, 2011.

(30) Foreign Application Priority Data

Dec. 23, 2011 (EP) .................................. 11195691

(51) Int. Cl.
| | |
|---|---|
| *C07C 51/48* | (2006.01) |
| *C12P 7/56* | (2006.01) |
| *B01D 11/04* | (2006.01) |
| *C07C 51/41* | (2006.01) |

(52) U.S. Cl.
CPC .............. *C07C 51/48* (2013.01); *B01D 11/04* (2013.01); *C07C 51/412* (2013.01); *C12P 7/56* (2013.01); *B01D 11/0426* (2013.01)

(58) Field of Classification Search
CPC ......... C07C 55/10; C07C 57/13; C07C 57/15; C07C 59/08; C07C 51/42; C07C 51/48; C07C 51/64; C07C 55/00–21; C07C 53/00–38; C07C 55/13; C07C 67/08; C07C 69/68; C07C 51/412; C12P 7/44; C12P 7/46; C12P 7/48; C12P 7/50; C12P 7/56; C12P 7/62; C30B 7/00; B01D 11/04; B01D 11/0426
USPC ....... 117/11, 68, 74; 435/135, 136; 560/179; 562/513

IPC ............. C30B 11/04,7/00; C07C 51/48, 67/08, 7/62

See application file for complete search history.

(56) References Cited

U.S. PATENT DOCUMENTS

| | | | |
|---|---|---|---|
| 2,710,880 A | 6/1955 | Filachione et al. | |
| 3,786,096 A | 1/1974 | Konno | |
| 4,275,234 A | 6/1981 | Baniel et al. | |
| 4,698,303 A | 10/1987 | Bailey et al. | |
| 5,104,492 A * | 4/1992 | King | C07C 51/48 203/15 |
| 5,426,219 A | 6/1995 | Lehnhardt et al. | |
| 6,229,046 B1 * | 5/2001 | Eyal | C07C 51/48 562/589 |
| 3,062,871 A1 | 11/2011 | Burgard et al. | |
| 9,422,217 B2 | 8/2016 | Kon et al. | |
| 2001/0014758 A1 * | 8/2001 | Baniel | C12P 7/56 562/580 |

(Continued)

FOREIGN PATENT DOCUMENTS

| | | |
|---|---|---|
| CN | 101979368 A | 2/2011 |
| CN | 102690189 A | 9/2012 |

(Continued)

OTHER PUBLICATIONS

Goswami et al. 2000. Fed-batch propionic acid production by Propionibacterium acidipropionici. Biochemical Engineering Journal, vol. 4:121-128.*

(Continued)

*Primary Examiner* — Thane Underdahl
(74) *Attorney, Agent, or Firm* — Oliff PLC

(57) ABSTRACT

A method for manufacturing carboxylic acid that includes the following steps is provided. First, subjecting an aqueous mixture, including carboxylic acid and at least 5 wt. % dissolved magnesium chloride, to a forward extraction step using a first organic liquid, including an organic solvent, the organic solvent being selected from the group of C5+ ketones, thereby obtaining an organic carboxylic acid solution and an aqueous waste liquid including magnesium chloride. Second, subjecting the organic carboxylic acid solution to a back extraction step wherein the carboxylic acid is extracted from the organic carboxylic acid solution into an aqueous liquid, thereby obtaining an aqueous carboxylic acid solution and a second organic liquid. Third, subjecting the aqueous waste liquid including magnesium chloride derived from the forward extraction to a thermal decomposition step at a temperature of at least 300° C., thereby decomposing the magnesium chloride to magnesium oxide and HCl.

25 Claims, 1 Drawing Sheet

(56) References Cited

U.S. PATENT DOCUMENTS

2007/0193960 A1    8/2007  Frank et al.

FOREIGN PATENT DOCUMENTS

| GB | 173 479 A | 11/1922 |
|---|---|---|
| GB | 280 969 A | 6/1928 |
| JP | H08-337552 A | 12/1996 |
| JP | H09-500649 A | 1/1997 |
| WO | 94/19307 A1 | 9/1994 |
| WO | WO 95/03268 A1 | 2/1995 |
| WO | WO 00/17378 A2 | 3/2000 |

OTHER PUBLICATIONS

Doi et al. 1988. Nuclear Magnetic Resonance Studies on Unusual Bacterial Copolyesters of 3-Hydroxybutyrate and 4-Hydroxybutyrate. Macromolecules, vol. 21:2722-2727.*
Dow Chemical Company 2002 MIBK Technical Data sheet.*
Britannica actic acid. Academic site. Printed Sep. 30, 2017.*
Hydrochloric Acid: Physical & Chemical Properties accessed at https://psa-hydrochloric-acid.weebly.com/physical--chemical-properties.html on Feb. 26, 2019, (Year: 2019).*
Sarangi et al. "Removal/recovery of hydrochloric acid using Alamine 336, Aliquat 336, TBP and Cyanex 923" Hydrometallurgy 84 (2006) 125-129 (Year: 2006).*
Hardinger "Illustrated Glossary of Organci Chemistry" excerpt from Keto and Ketone 4 page copy right 2010-2017. (Year: 2010).*
NIOSH "isoamyl alcohol" 2 pages 2019 (Year: 2019).*
NIOSH "dissopropyl ether" 2 pages 2019 (Year: 2019).*
Kopeliovich, "Classification of Solvents" available online Jun. 2, 2012, 2 pages (Year: 2012).*
International Search Report issued in International Patent Application No. PCT/EP2012/076741 dated Mar. 27, 2013.
Written Opinion of International Searching Authority issued in International Patent Application No. PCT/EP2012/076741 dated Mar. 27, 2013.
Aug. 18, 2015 Office Action Issued in Korean Patent Application No. 10-2014-7020313.
Kailas L. Wasewar et al. "Equilibrium Study for Reactive Extraction of Caproic Acid in Mibk and Xylene." Department of Chemical Engineering Visvesvaraya National Institute of Technology. 2001 vol. 3 pp. 829-835.
Apr. 1, 2016 Office Action issued in Korean Patent Application No. 10-2014-7020313.
Jun. 1, 2016 Office Action issued in Vietnamese Patent Application No. 1-2014-02254.
Apr. 28, 2016 Office Action issued in Ukranian Patent Application No. a 2014 07598.
Substantial, Definition of Substantial by Merriam-Webster, May 21, 2016, 1 page, http://www.merriam-webster.com/dictionary/substantial.
G. Jurriens el al., "Analysis of Calcium Salts of Fatty Acid-Lactic Acid Condensates," Calcium Salts of Acid Condensates, vol. 43, Nov. 1966, pp. 669-674.
Jun. 30, 2016 Office Action issued in U.S. Appl. No. 14/368,595.
May 4, 2017 U.S. Office Action Issued in U.S. Appl. No. 14/366,595.
Oct. 18, 2016 Office Action Issued In U.S. Appl. No. 14/366,620.
Jan. 11, 2018 Office Action issued in Indian Application No. 5067/CHENP/2014, 6 pgs.
May 22, 2019 Office Action issued in Brazilian Patent Application No. BR112014014882-1.
PubChem "Methyl Ethyl Ketone" 4 pgs, accessed Feb. 22, 2018 (Year: 2018).
Mar. 7, 2019 Office Action Issued in U.S. Appl. No. 14/366,628.
Mar. 1, 2016 Office Action Issued In U.S. Appl. No. 14/366,620.
Koopman et al.; "Efficient whole-cell biotransformation of 5-(hydroxymethyl)furfural into FDCA, 2,5-furandicarboxylic acid;" Bioresource Technology; 2010; pp. 6291-6296; vol. 101.
Apr. 8, 2013 International Search Report issued in International Patent Application No. PCT/EP201/076696.
Apr. 8, 2013 Written Opinion issued in International Patent Application No. PCT/EP2012/076696.
Apr. 16, 2013 International Search Report issued in International Patent Application No. PCT/EP2012/076735.
Apr. 16, 2013 Written Opinion issued in International Patent Application No. PCT/EP2012/076735.
Nov. 11, 2015 Office Action issued in Japanese Patent Application No. 2014-548085.
Nov. 11, 2015 Office Action issued in Japanese Patent Application No. 2014-548084.
Nov. 10, 2015 Office Action issued in Japanese Patent Application No. 2014-548079.
U.S. Appl. No. 14/366,620, filed Jun. 18, 2014 in the name of De Haan et al.
U.S. Appl. No. 14/366,595, filed Jun. 18, 2014 in the name of De Haan et al.
Oct. 15, 2015 Election of Species Requirement issued in U.S. Appl. No. 14/366,620.
Oct. 21, 2015 Office Action issued in U.S. Appl. No. 14/366,595.
Oct. 4, 2017 Office Action Issued In U.S. Appl. No. 14/366,620, 17 pgs.

\* cited by examiner

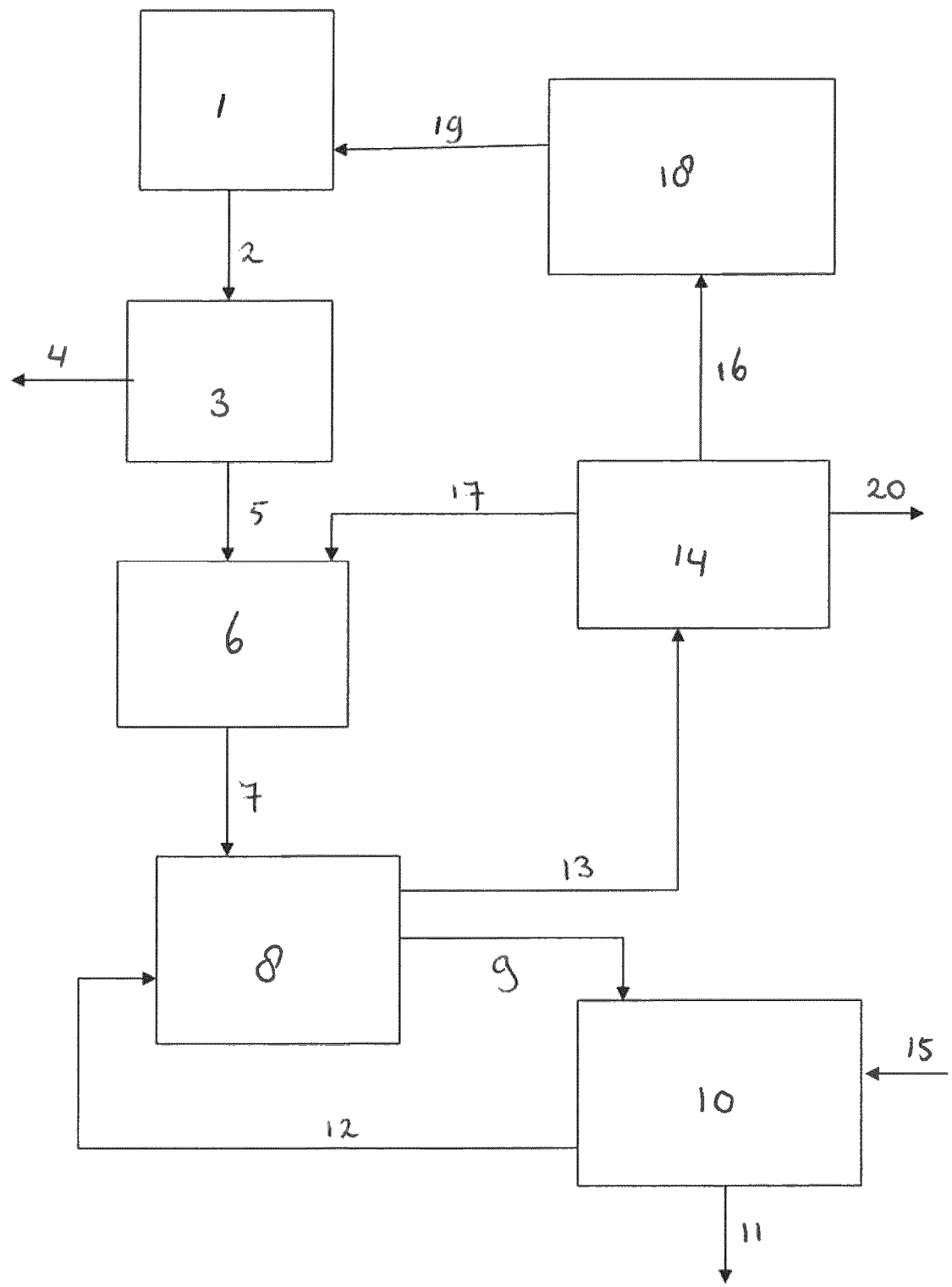

METHOD FOR ISOLATING A CARBOXYLIC ACID FROM AN AQUEOUS SOLUTION

RELATED APPLICATIONS

This application claims the benefit of International Application No. PCT/EP2012/076741 filed Dec. 21, 2012, which claims the benefit of U.S. Provisional Application No, 61/579,730 filed Dec. 23, 2011.

The invention is directed to a method for manufacturing a carboxylic acid through an integrated process.

Carboxylic acids can be manufactured via fermentation of a carbon source, such as carbohydrates or glycerol, by micro-organisms. In such a fermentation process a carbohydrate source is typically fermented by means of a micro-organism to form a carboxylic acid. The liquid wherein the carbohydrate source is fermented is called the fermentation broth or the fermentation medium.

The formation of carboxylic acid during fermentation will result in a decrease of the pH of the fermentation broth. Since such a decrease in pH can damage the micro-organism's metabolic process, it is common practice to add a neutralizing agent, i.e. a base, in the fermentation media in order to neutralize the pH. As a result, carboxylic acid produced in the fermentation media is typically present in the form of a carboxylate salt. Although there are micro-organisms that are to some extent resistant to acidic environments, such that fermentation can be conducted at a low pH (e.g. at a pH of 3), even in these processes at least part of the carboxylic acid is obtained as a carboxylate salt.

To recover the carboxylic acid from the fermentation broth after fermentation, downstream processing is required. In such processing, the carboxylate salt in the fermentation broth needs to be converted into carboxylic acid. Also, the carboxylic acid (or carboxylate if not yet converted) needs to be isolated from the fermentation broth. Since a fermentation broth comprises many compounds, including significant amounts of biomass (such as micro-organisms) and salt (originating from the neutralizing agent), recovering and isolating carboxylic acid can be rather complex, typically requiring multiple processing steps and leading to waste material, in particular salt waste.

WO0017378 describes a process for preparing lactic acid, which proposes to address these deficiencies. In the process of this reference lactic acid is manufactured by fermentation with the pH during fermentation being adjusted with, e.g., magnesium hydroxide to form magnesium lactate. The magnesium lactate is reacted with HCl in an aqueous medium to form a reaction mixture comprising lactic acid and dissolved magnesium chloride. The acid is recovered from the salt solution via forward extraction with an organic liquid, followed by back extraction of the organic acid solution using water, to form a product lactic acid solution. The extraction solvent is selected from amines, alcohols, and ethers, preferably isoamyl alcohol, diisopropyl ether, and Alamine 336. The remaining magnesium chloride solution can be subjected to a thermolysis step, where the magnesium chloride is converted into magnesium oxide powder and hydrochloric acid. The magnesium oxide powder is converted to magnesium hydroxide, which is recycled to the fermentation step. The hydrochloric acid is recycled to the acidification step. The process of this reference is quite attractive on paper, because it makes it possible to recycle the magnesium and the chloride, thus preventing the formation of waste salt. However, the process as described in WO0017378 is not as such suitable for commercial operation, for a number of reasons.

It has appeared that a substantial amount of extraction solvent ends up in the salt solution provided to the thermohydrolysis step. This is disadvantageous, not only because solvent loss is as such undesirable, but also because the incineration of organic components in an atmosphere which also contains chlorine has the risk of the formation of undesirable side products.

It has further appeared that the product aqueous acid solution formed in WO00/17378 contains undesirable contaminants, which are moreover difficult to remove.

There is therefore need for an adapted version of the process described in WO00/17378 which does not suffer from the above disadvantages. The present invention provides such a process.

The present invention is directed to a method for manufacturing carboxylic acid comprising the steps of
  subjecting an aqueous mixture comprising carboxylic acid and at least 5 wt. % dissolved magnesium chloride, based on the total weight of water and dissolved material in the aqueous mixture to a forward extraction step wherein the carboxylic acid is extracted from the aqueous mixture into a first organic liquid comprising an organic solvent, the organic solvent being selected from the group of C5+ ketones, thereby obtaining an organic carboxylic acid solution and an aqueous waste liquid comprising magnesium chloride,
  subjecting the organic carboxylic acid solution to a back extraction step wherein the carboxylic acid is extracted from the organic carboxylic acid solution into an aqueous liquid, thereby obtaining an aqueous carboxylic acid solution and a second organic liquid,
  subjecting the aqueous waste liquid comprising magnesium chloride derived from the forward extraction to a thermal decomposition step at a temperature of at least 300° C., thereby decomposing the magnesium chloride to magnesium oxide and HCl.

The crux of the present invention resides in the selection of a specific solvent in the extraction step. It has been found that the use of a C5+ ketone results in the formation of an end product aqueous carboxylic acid solution which contains less impurities, and which can also be easier purified than the solutions manufactured using the solvents described in WO00/17378. Further, the liquid provided to the thermal decomposition process also contains less organic compounds, and the compounds present therein are less harmful. Both make for a thermal decomposition process that can be operated under HSE-acceptable conditions without requiring extensive apparatus.

Not wishing to be bound by theory it is believed that the solvents described in WO0017378 have the following disadvantages. Due to their basic nature, both the ethers and the amines have relatively high affinity for the salt solution, making for a relatively high concentration of these solvents in the salt solution to be provided to the thermal decomposition step, where they may cause the formation of undesirable side products by incomplete decomposition. For amines as solvent there is the additional risk of the formation of NOx compounds, which necessitates additional apparatus. For ethers their provision to a thermal decomposition step entails explosion risks. Further, for the same reason, their basic nature, ethers and amines will end up in the product aqueous acid solution in relatively large amounts. Amines in particular are difficult to remove therefrom. Further, it has been found that these compounds also lead to an increased chloride concentration in the product, due to acid-base interaction of the amine or ether with HCl. Not only are chloride compounds difficult to remove, their presence also places heavy requirements on process equipment due to their corrosive nature.

The alcohols mentioned in WO0017378 lead to the formation of side products, because they react with the acid. The side products end up in the end product, from which they are difficult to remove. The short-chain alcohols have a high solubility in water, resulting in their ending up in the feed for the thermal decomposition step and in the product. The long chain alcohols are less likely to end up in the product, but if they do, they are difficult to remove.

It has been found that the selection of a specific group of solvents, namely the C5+ ketones, these problems do not occur. Further advantages for specific embodiments of the invention will be discussed below.

The present invention is suitable for the manufacture of carboxylic acids. In one embodiment the carboxylic acid is a mono-, di- or tri-carboxylic acid comprising at least 2, but no more than 6 carbon atoms (C2-6 carboxylic acid). In one embodiment, the carboxylic acid is selected from the group consisting of lactic acid, succinic acid, propionic acid, 3-hydroxypropionic acid, 2-, 3-, and 4-hydroxybutyric acid, citric acid, fumaric acid, itaconic acid, adipic acid, acrylic acid, levulinic acid, maleic acid, 2,5-furandicarboxylic acid, mandelic acid, malic acid, and tartartic acid. Preferably, the carboxylic acid is selected from the group consisting of lactic acid, succinic acid, propionic acid, 3-hydroxypropionic acid, 2-, 3-, and 4-hydroxybutyric acid and citric acid.

In one embodiment, the carboxylic acid is selected from the mono-carboxylic acids with 2-6 carbon atoms. In one embodiment, the monocarboxylic acid with 2-6 carbon atoms does not contain hydroxyl-groups. Within this group, examples of suitable acids are propionic acid, acrylic acid, butyric acid, and valeric acid.

In another embodiment, the monocarboxylic acid contains at least one hydroxyl-group. Within this group, in one embodiment it may be preferred to select the acid from the group of lactic acid, glycolic acid, 3-hydroxypropionic acid, 2-, 3-, and 4-hydroxybutyric acid. In another embodiment within this group it may be preferred to select the acid from the group of glycolic acid, 3-hydroxypropionic acid, and 2-, 3-, and 4-hydroxybutyric acid. In a further embodiment it may be preferred for the acid to be lactic acid.

In another embodiment, the carboxylic acid is a polycarboxylic acid, more in particular a di- or tri-carboxylic acid comprising at least 2, but no more than 6 carbon atoms (C2-6 carboxylic acid). In one embodiment, the polycarboxylic acid is selected from the group consisting of succinic acid, citric acid, fumaric acid, itaconic acid, adipic acid, maleic acid, 2,5-furandicarboxylic acid, mandelic acid, malic acid, and tartartic acid. Preferably, the polycarboxylic acid is selected from the group consisting of succinic acid, citric acid, fumaric acid, itaconic acid, adipic acid, and 2,5-furandicarboxylic acid. The polycarboxylic acid may in particular be selected from succinic acid, fumaric acid, itaconic acid, and 2,5-furandicarboxylic acid.

In the process according to the invention, a mixture comprising carboxylic acid and magnesium chloride is subjected to the combination of a forward extraction step and a back extraction step. In the process according to the invention, these steps are carried out by subjecting an aqueous mixture comprising carboxylic acid and at least 5 wt. % dissolved magnesium chloride, based on the total weight of water and dissolved material in the aqueous mixture to a forward extraction step wherein the carboxylic acid is extracted from the aqueous mixture into a first organic liquid comprising an organic solvent, thereby obtaining an organic carboxylic acid solution and an aqueous waste liquid comprising magnesium chloride, subjecting the organic carboxylic acid solution to a back extraction step wherein the carboxylic acid is extracted from the organic carboxylic acid solution into an aqueous liquid, thereby obtaining an aqueous carboxylic acid solution and a second organic liquid.

Not wishing to be bound by theory, it is believed that one or more of the following effects may occur in the extraction process in the method according to the invention.

It may be that the presence of the magnesium chloride in the aqueous mixture enhances the extraction of the carboxylic acid from the aqueous mixture into the first organic liquid. Second, it may be that the dissolved magnesium chloride decreases the solubility of the organic solvent in water. In particular, at higher concentrations of dissolved magnesium chloride, less solvent might dissolve in the aqueous mixture. This effect may be stronger at higher temperatures, in particular in the temperature range of 20° to 100° C. Accordingly, forward and/or back extraction are preferably conducted at a temperature of at least 25° C., preferably at least 30° C., more preferably at least 40° C. The lower solubility of the organic liquid in water will result in streams with higher purity and less solvent losses in both the forward and back extraction and may thus lead to a more efficient process. In contrast, the solubility of water in alcohol and the solubility of alcohol in water increases when increasing the temperature in temperature range of 25° C. and 100° C.

Third, the solubility of the water in the organic solvent during extraction may also be decreased by the presence of the dissolved magnesium chloride.

Fourth, it was found that dissolved magnesium chloride may suppress emulsion formation, thereby enhancing phase-separation between the aqueous and organic liquids. This is in particular advantageous when the aqueous mixture comprises traces of biomass. Biomass originating from a fermentation process typically comprises compounds that can act as surfactants. Consequently, when an aqueous mixture comprising biomass is brought into contact with an organic solvent, typically an emulsion will be formed. Such emulsion formation is undesirable, because it may disrupt the extraction process and phase separation.

The aqueous mixture comprises at least 5 wt. % dissolved magnesium chloride. To increase the efficiency of the extraction step in the process according to the invention it is preferred for larger amounts of dissolved magnesium chloride to be present in the aqueous mixture. Therefore, the concentration of the magnesium chloride dissolved in the aqueous mixture is preferably as high as possible. The aqueous mixture preferably comprises at least 10 wt. %, more preferably at least 15 wt. % of the magnesium chloride, based on the total weight of water and dissolved material in the aqueous mixture (i.e. the total weight of the aqueous mixture excluding any solid matter). Even more preferably the aqueous mixture comprises at least 20 wt. %, even more preferably at least 25 wt. % of dissolved magnesium chloride. It may be possible to use at least 30 wt. %, even more preferably at least 35 wt. % dissolved magnesium chloride, based on the total weight of the aqueous mixture. The maximum value is generally determined by the solubility of magnesium chloride, which is about 45 wt. %.

Preferably, the aqueous mixture has a dissolved magnesium chloride concentration that is as high as possible, i.e. close to the solubility of the magnesium chloride, i.e. close to the maximum weight amount of the magnesium chloride that can be dissolved in the aqueous mixture, measured at the temperature at which forward extraction is conducted.

Although undissolved magnesium chloride may be present in the aqueous mixture, this is not desirable. Therefore, the salt concentration in the aqueous mixture is preferably not higher than the solubility of the magnesium chloride in the aqueous mixture, so as to prevent precipitation. Accordingly, in one embodiment the aqueous mixture has a dissolved magnesium chloride concentration within 10 wt. %, preferably within 5 wt. % of the solubility of the magnesium chloride in the aqueous mixture. Dissolved magnesium chloride as used herein refers to magnesium chloride in its dissolved state, i.e. in the form of solvated ions, in water.

In this respect, it is noted that fermentation broths generally have a magnesium chloride concentration in the order of 0.1 wt. % (before adding inorganic salts, such as neutralizing agents). Even when such a broth is concentrated after fermentation, the magnesium chloride concentration will be lower than 5 wt. %. The magnesium chloride present in the mixture to be extracted will therefore not be present in the fermentation broth as such; it generally originates from the addition of HCl during an acidification step, and optionally from the addition of additional magnesium chloride and/or from a concentration step.

The term "extraction" as used herein refers to liquid-liquid extraction, also known as solvent extraction. Solvent extraction is an extraction method based on the difference in solubility of a compound in two different liquids, i.e. in the present case the solubility of the carboxylic acid in water (present in the aqueous mixture and the aqueous liquid) relative to the solubility of the carboxylic acid in the organic solvent (present in the organic liquid). Forward extraction is the process wherein the compound to be extracted is extracted from the aqueous mixture into the organic liquid. Back extraction is the process wherein the compound to be extracted is extracted from the organic liquid into an aqueous liquid.

The term "solubility" as used herein refers to the maximum weight amount of a compound that can be dissolved in a certain amount of an aqueous mixture at a certain temperature.

Forward extraction and back extraction as used in the method of the invention are based on the difference in solubility of the carboxylic acid in water and the organic solvent at different temperatures. The solubility of a compound in one solvent relative to another solvent can be expressed in terms of the distribution ratio (DR). This ratio gives an indication how a compound will be distributed over the aqueous phase (e.g. the aqueous mixture) and the organic phase (e.g. the organic liquid) in a two-phase system at equilibrium. The distribution ratio may be defined as the ratio of the carboxylic acid concentration dissolved in the organic phase ([carboxylic acid]$_{organic}$) over the concentration of the carboxylic acid dissolved in water ([carboxylic acid]$_{water}$), provided that the two phases are in equilibrium with each other:

$$DR = [\text{carboxylic acid}]_{organic} / [\text{carboxylic acid}]_{water} \quad (1)$$

From formula (1) it can be concluded that the higher the distribution ratio, the more carboxylic acid will dissolve in the organic phase.

The distribution ratio depends on many variables, including the temperature and the specific composition of the organic and water phase. For example, the concentration of the dissolved magnesium chloride in the aqueous mixture and the type of solvent used will influence the distribution ratio. During forward extraction, the carboxylic acid should preferably dissolve better in the organic solvent than in water. Consequently, the distribution ratio in the forward extraction should be as high as possible. In particular, a high distribution ratio during forward extraction is desirable as any carboxylic acid still present in the waste liquid will directly lead to a decrease of the total carboxylic acid yield when this waste liquid cannot be reworked and/or recycled back to the process again, or used for other purposes and should be disposed off. In case the distribution ratio during forward extraction is high, relatively little carboxylic acid will be lost since most of the carboxylic acid will have been dissolved in the organic liquid.

It is preferred for the DR in forward extraction, also indicated as $D_{FE}$ to be at least 0.1, more in particular at least 0.4, still more in particular at least 0.8.

During back extraction, the opposite holds true. The carboxylic acid should preferably dissolve better in the aqueous phase than in the organic liquid. It is preferred for the DR in the backward extraction, also indicated as also indicated as $D_{BE}$ to be at most 0.5, more in particular at most 0.3, still more in particular at most 0.1.

If the distribution ratio for forward extraction is higher than the distribution ratio for back extraction, this will contribute to a concentration effect, wherein the aqueous carboxylic acid solution obtained after back extraction has a higher concentration of carboxylic acid than the aqueous mixture used as starting material in the forward extraction. To achieve a concentration effect it is preferred for the ratio between $D_{FE}$ and $D_{BE}$ to be at least 1.1, more in particular at least 2. The ratio between $D_{FE}$ and $D_{BE}$ will generally not be more than 10.

The method of the invention comprises the step of providing an aqueous mixture comprising carboxylic acid and dissolved magnesium chloride. The aqueous mixture is the mixture to be extracted with the organic liquid.

The aqueous mixture is preferably an aqueous solution, since extraction can be more easily conducted when no solid matter is present. Such a solution may be referred to as an aqueous feed solution. Nevertheless, the presence of solid matter in the aqueous mixture is possible to a certain extent, dependent on the equipment used, as will be evident to the skilled person. Thus, the aqueous mixture can also be a suspension. Examples of solid matter that can be present in such a suspension are carboxylic acid in solid form, undissolved magnesium chloride and insoluble impurities.

The carboxylic acid content present in the aqueous mixture is preferably as high as possible. Depending on the solubility of the acid, the aqueous mixture may comprise for example at least 5 wt. %, preferably at least 10 wt. %, more preferably at least 15 wt. % carboxylic acid, based on the total weight of the aqueous mixture. The water present in the aqueous mixture may be saturated with carboxylic acid. The aqueous mixture may comprise carboxylic acid in solid form, but preferably the solid content is as low as possible as solids may create a more challenging extraction and phase separation. It is within the scope of the skilled person to determine the type of commercially available extraction equipment able to handle solids. Accordingly, the carboxylic acid content in the aqueous mixture is may be higher, but is preferably equal to or lower than the solubility of the carboxylic acid in the aqueous mixture. Preferably, more than 99 wt. % of the carboxylic acid present in the aqueous mixture is in dissolved form.

In one embodiment, the aqueous mixture has a pH of 2 or lower, typically a pH below 1, for example a pH of 0-1. It is preferred for the pH to be relatively low, to ensure that the carboxylic acid is present in the mixture in acidic form, allowing extraction.

The aqueous mixture may further comprise impurities, in particular impurities originating from the fermentation process. Such impurities may be soluble or insoluble in the aqueous mixture. Examples of dissolved impurities are sugars, proteins, and salts. Insoluble biomass (e.g. microorganisms) and insoluble salts are examples of insoluble impurities. These impurities may all be typically present in a fermentation broth.

In certain embodiments, it may be preferred that the carboxylic acid has a solubility in water that is higher than that of the magnesium chloride, wherein the solubility is defined as the maximum weight amount of a compound that can be dissolved in 100 g water at 20° C. Thus, it is possible to dissolve a larger amount of carboxylic acid in the aqueous mixture than the amount of dissolved magnesium chloride without occurrence of precipitation of the magnesium chloride or carboxylic acid. For example, in case $MgCl_2$ is used as the dissolved magnesium chloride, the carboxylic acid preferably has a solubility in water of more than 60 g/100 g water at 20° C., preferably more than 80 g/100 g, even more preferably 100 g/100.

In the method according to the invention, the aqueous mixture discussed above is subjected to an extraction step by contacting it with an organic liquid comprising an organic solvent selected from the group of C5+ ketones, thereby obtaining an organic carboxylic acid solution and an aqueous waste liquid comprising magnesium chloride. In this forward extraction, the carboxylic acid is separated from the impurities present in the aqueous mixture by dissolving it in the first organic liquid. The impurities will remain in the aqueous mixture.

Preferably, the organic liquid comprises at least 90 wt. % of the organic solvent, preferably at least 95 wt. %, more preferably at least 99 wt. %. In one embodiment, the organic liquid is the organic solvent. Typically, small amounts of water can be present in the first organic liquid, in particular when the liquid (partly) comprises recycled organic solvent from a recycle step after extraction.

The organic solvent is selected from the group of C5+ ketones. C5+ stands for ketones with at least 5 carbon atoms. It has been found that specific solvents compounds show good properties in the process according to the invention, in particular as regards the purity or purification ability of the end product, and as regards the composition of the waste liquid to be provided to the thermal decomposition step. In some embodiments, the use of this solvent is associated with a concentration effect occurring, where the concentration of acid in the end product is higher than the concentration of acid in the starting mixture. Selection of a suitable organic solvent may contribute to establishing a high distribution ratio during forward extraction. In that case, only a relatively small amount of carboxylic acid will be lost in the aqueous waste liquid.

In the present invention it is preferred to use C5-C8 ketones. Mixtures may also be used. The use of C9+ ketones is less preferred, because these compounds may result in more contaminants in the end product. The use of methylisobutylketone (MIBK) has been found to be particularly attractive.

The extraction step in the method of the invention does not require the use of extracting agents, such as amines. In fact, the use of extracting agents in the organic solvent is generally undesirable. An extracting agent is a compound that forms a complex with the compound to be extracted (in this case carboxylic acid). However, the formation (during forward extraction) and breakage of the complex would require a relatively large amount of energy, such that the difference in temperature between forward and back extraction would need to be larger than necessary. Accordingly, the organic liquid preferably comprises no or substantially no extracting agents, in particular no or substantially no amine extracting agents. Thus, the carboxylic acid in the method of the invention is preferably extracted in its neutral acidic form and not in the form of a salt or a complex.

The organic liquid is preferably essentially free of amines, ethers, and alcohols, which means that these compounds, if present at all, are each present in an amount of less than 2 wt. %, preferably less than 1 wt. %, more preferably less than 0.5 wt. %, calculated on the weight of the organic liquid.

The ratio of organic liquid to aqueous mixture used in forward extraction is determined by the following considerations. On the one hand, if the amount of organic liquid is relatively high, the efficiency of the extraction, expressed as the percentage of acid in the aqueous mixture which is extracted into the organic liquid will be high. On the other hand, a large amount of organic liquid will have to be used. Conversely, if the amount of organic liquid is relatively low, less organic liquid is required, but the extraction efficiency will be reduced.

The Distribution Ratio (DR) defined above can give guidance in this respect.

In one embodiment, the amount of organic liquid used in the forward extraction may be in the range of 0.5/DR to 1.5/DR times the amount of aqueous mixture.

The use of an amount of organic liquid in the range of 0.5/DR to 0.8/DR times the amount of aqueous mixture for forward extraction may be desirable to reduce the amount of solvent used, and will help to increase the concentration of acid in the final product. However, the yield of the extraction step may in this case be less than 99%.

The use of an amount of organic liquid in the range of 1.3/DR to 1.5/DR times the amount of aqueous mixture for forward extraction may result in an extraction yield of over 99%, but may lead to a reduction of the concentration of the acid in the final product. The use of an amount of organic liquid in the range of 0.8/DR to 1.3/DR, and in particular in the range of 1.0/DR to 1.2/DR, times the amount of aqueous mixture for forward extraction is most desirable, because in this range both an optimum concentration of acid in the product and an extraction yield of over 99% can be obtained. The extraction yield as used herein refers to the weight percentage of the carboxylic acid that is extracted into the organic liquid during forward extraction.

Forward extraction is typically conducted by contacting the aqueous mixture with the first organic liquid, thereby obtaining an organic carboxylic acid solution and an aqueous waste liquid comprising the magnesium chloride. Preferably, the extraction is a counter-current extraction, i.e. the aqueous mixture and organic liquid are contacted with each other using counter-current streams. In such a configuration, a very efficient extraction of carboxylic acid into the organic liquid can be obtained, in particular with respect to the yield.

The extraction is preferably conducted in an extraction column. In case the organic solvent used has a lower density than water (for example in case of MIBK), the organic solvent is preferably fed to the bottom of the column, while the aqueous mixture is fed at the top of the column.

Consequently, two phases will form: an upper phase comprising the organic solvent and a lower phase comprising the aqueous mixture. At the interface of the two phases, any biomass and/or other solid matter present in the aqueous mixture will accumulate. As described above, the biomass does not cause emulsification due to the presence of the salt in the aqueous mixture. By feeding the organic solvent at the bottom of the column, the organic solvent will move upwards through the aqueous mixture, thereby extracting the carboxylic acid and forming an organic carboxylic acid solution. At the bottom of the column, an aqueous waste liquid can be obtained, typically in the form of an aqueous salt solution, which solution comprises the magnesium chloride.

Forward extraction may be conducted at a temperature of 20-100° C., preferably at a temperature of 30-80° C., for example at a temperature of 40-60° C. To reach the desirable temperature for forward extraction, the aqueous mixture and/or organic liquid may be heated prior to forward extraction. As described above, higher temperatures within the range of 20-100° C. are advantageous with respect to a decrease in solubility of the organic solvent in water. In addition, the distribution ratio may increase with increasing temperatures and/or may lead to an increased concentration of carboxylic acid in the product. In view of the possible corrosive conditions of the acidic aqueous mixture, a temperature above 60° C. may be disadvantageous. However, corrosion may for example be avoided by using plastic or glass-lined extraction equipment.

The aqueous waste liquid formed in the forward extraction comprises the magnesium chloride. The aqueous waste liquid is typically obtained in the form of an aqueous salt solution, which solution comprises the magnesium chloride. This solution is relatively pure, since insoluble impurities typically remain at the interface of the water/organic interface during extraction.

To prevent acid loss from the system, it is preferred for the concentration of polycarboxylic acid in the waste liquid to be as low as possible. In one embodiment, the polycarboxylic acid concentration in the waste liquid is below 1 wt. %, in particular below 0.5 wt. %, more in particular below 0.1 wt. %. It has been found that extraction using the method according to the invention allows obtaining these very low acid losses. To prevent solvent loss from the system, and to prevent problems in further processing, in particular when use is made of a thermal decomposition step, it is preferred for the concentration of solvent in the waste liquid to be as low as possible. In one embodiment, the solvent concentration in the waste liquid is below 1 wt. %, in particular below 0.5 wt. %, more in particular below 0.2 wt. %, and preferably below 0.1 wt. %. It has been found that extraction using the method according to the invention allows obtaining these very low solvent losses.

It is preferred for at least 80% of the acid present in the system to be in the organic phase after the forward-extraction, in particular at least 90%, preferably at least 95%, more preferably at least 98%, still more preferably at least 99%.

It is preferred for at least 90% of the magnesium chloride present in the system to be present in the aqueous waste liquid after the forward extraction, preferably at least 95%, more preferably at least 98%, in particular at least 99%.

The organic carboxylic acid solution is subsequently submitted to a back extraction step. Optionally, the organic carboxylic acid solution obtained in the forward extraction is subjected to an intermediate washing step to remove any impurities present in the organic carboxylic acid solution. Such impurities are typically entrained from the aqueous mixture, for example chloride or metal ions. In such a washing step, the organic carboxylic acid solution is contacted with a washing liquid. Such a step may decrease the amount of impurities, such as chloride and/or metal ions in the end product, i.e. the aqueous carboxylic acid solution. The removal of these ions may further prevent corrosion problems. The washing liquid is typically an aqueous liquid. In one embodiment, part of the aqueous carboxylic acid solution formed as product in the back extraction is used as the washing liquid. In this embodiment, a small part, for example 0.5-5 wt. %, in particular 0.5-2 wt. %, of the product total aqueous carboxylic acid solution may be used for washing. The washing liquid may subsequently be recycled back to the aqueous mixture, where it will again be subjected to forward extraction. Care should be taken during washing not to remove too much acid from the organic liquid, as this will detrimentally affect the concentration of carboxylic acid in the final product. It is within the scope of the skilled person to determine suitable washing conditions.

The organic carboxylic acid solution formed in the forward extraction is, optionally after being washed, back extracted into an aqueous liquid, thereby obtaining an aqueous carboxylic acid solution and a second organic liquid. This step may be referred to herein as the second extraction or back extraction. The back extraction results in an aqueous carboxylic acid solution, which has a higher purity and in particular a lower salt concentration than the initial aqueous mixture. Further, in some embodiments of the invention, as explained above, the product aqueous carboxylic acid solution of the present invention has a higher concentration of carboxylic acid than the aqueous mixture.

The ratio of aqueous liquid to organic acid solution used in the back extraction is determined by the following considerations. On the one hand, if the amount of aqueous liquid is relatively high, the efficiency of the extraction, expressed as the percentage of acid in the organic acid solution which is extracted into the aqueous liquid will be high. On the other hand, a large amount of aqueous liquid will have to be used, and the concentration of the carboxylic acid in the final product will decrease. Conversely, if the amount of aqueous liquid is relatively low, the concentration of carboxylic acid in the final product will be improved, but the extraction efficiency will be reduced.

A suitable value for the ratio of aqueous liquid to organic acid solution used in that back extraction may be derived from the Distribution Ratio (DR) defined above. In one embodiment, the amount of aqueous liquid used in the back extraction is 0.5*DR to 1.5*DR times the amount of the organic carboxylic acid solution.

The use of an amount of aqueous liquid in the range of 0.5*DR to 0.8*DR times the amount of organic carboxylic acid solution for back extraction may be desirable for obtaining a high concentration of carboxylic acid in the final product. However, the yield of the back extraction step may in this case be less than 99% yield. The use of an amount of aqueous liquid in the range of 1.3*DR to 1.5*DR times the amount of organic carboxylic acid solution for back extraction may result in a back extraction yield of over 99%, but typically leads to a reduction of the carboxylic acid concentration in the final product. The use of an amount of aqueous liquid in the range of 0.8*DR to 1.3*DR, and in particular in the range of 1.0*DR to 1.2*DR times the amount of organic carboxylic acid solution is most desirable, because in this range both an optimum concentration of acid in the product and an extraction yield of over 99% can be obtained. The back extraction yield as used herein refers to the weight percentage of the carboxylic acid that is extracted into the aqueous liquid during back extraction.

Back extraction is typically conducted by contacting the organic carboxylic acid solution with the aqueous liquid, thereby obtaining an aqueous carboxylic acid solution and a second organic liquid. The aqueous carboxylic acid solution is the product solution. If so desired, the second organic liquid, in its entirety or in part, may be recycled to the forward extraction as first organic liquid, optionally after having been subjected to a purification step. Preferably, the extraction is a counter-current extraction. In such a configuration, a very efficient extraction of carboxylic acid into the aqueous liquid can be obtained, in particular with respect to the yield.

The extraction is preferably conducted in an extraction column. In case the organic solvent used has a lower density than water, the aqueous liquid is preferably fed at the top of the column, while the organic carboxylic acid solution is fed at the bottom of the column. Consequently, two phases will form: an upper phase comprising the organic solvent and a lower phase comprising the aqueous liquid. By feeding the aqueous liquid at the top of the column, it will pass downward through the organic carboxylic acid solution, thereby extracting the carboxylic acid and forming an aqueous carboxylic acid solution. An aqueous carboxylic acid solution can then be recovered at the bottom of the column.

It is noted that it was contemplated to evaporate the organic solvent from the organic carboxylic acid solution after forward extraction, thereby directly obtaining the carboxylic acid. However, better results were obtained when using a back extraction in accordance with the present invention. Back extraction resulted in less impurities and a more energy efficient process.

Back extraction may be conducted at a temperature of 20-100° C., preferably at a temperature of 80° C. or lower, more preferably at a temperature of 60° C. or lower. Back extraction is preferably conducted at a temperature above 0° C., preferably a temperature of at least 10° C. due to energy costs associated with cooling. Temperatures equal or close to the temperature in the forward extraction are particular preferred for back extraction. This may save energy, because less heating and/or cooling is required between the different streams in the extraction process. Accordingly, in one embodiment the back extraction is conducted at a temperature that is within 10° C., for example within 5° C. of the temperature at which forward extraction is conducted. The use of a similar temperature in forward and back extraction is herein also referred to as isothermal conditions.

Forward extraction and back extraction may be conducted at about the same temperature, for example using a temperature difference between forward and back extraction of less than 5° C.

In one embodiment, the extraction into the organic liquid (forward extraction) is conducted at a lower temperature than the extraction into the aqueous liquid (back extraction). Such an extraction method is also known as a regular temperature swing extraction. The temperature during back extraction is in this case 5-45° C., for example 10-20° C. higher than the temperature in forward extraction.

In another embodiment, the extraction into the organic liquid (forward extraction) is conducted at a higher temperature than the extraction into the aqueous liquid (back extraction). Such an extraction method may be indicated as a reverse temperature swing extraction. In the reverse temperature swing extraction, the back extraction step may in this case be conducted at a temperature that is 10-50° C. or 20-30° C. lower than the temperature at which forward extraction is conducted. It has been found that operating extraction in reverse temperature swing mode may lead to an increased concentration of acid in the product.

In one embodiment in the process according to the invention the organic carboxylic acid solution is brought into thermal contact with the second organic liquid using a heat exchanger. This is advantageous when forward and back extraction are conducted at different temperatures.

It has been found that in some embodiments of the invention the aqueous carboxylic acid solution obtained after back extraction as performed according to the present invention has a higher carboxylic acid concentration than the aqueous mixture which was fed to the forward extraction.

Whether or not this effect occurs, and if so, to what extent depends i.a. on the nature of the acid, the ratio of the organic liquid and aqueous mixture used in forward extraction, the ratio of the aqueous liquid and organic carboxylic acid solution used for back extraction, the temperature at which the extraction steps are conducted, the type of organic liquid used and the amount of dissolved magnesium chloride present in the aqueous mixture.

Furthermore, it is preferred to select the process conditions in such a manner that so as to obtain a high extraction yield. In this respect, it is preferred that the weight amount of organic liquid used in forward extraction is 1.0/DR to 1.2/DR times the weight amount of aqueous mixture while the weight amount of aqueous liquid used in back extraction is 1.0*DR to 1.2*DR times the weight amount of organic carboxylic acid solution. It is even more preferred that the weight amount of organic liquid used in forward extraction is 1.1/DR to 1.2/DR times the weight amount of aqueous mixture while the weight amount of aqueous liquid used in back extraction is 1.1*DR to 1.2*DR times the weight amount of organic carboxylic acid solution. These weight ratios result in a particular good concentration effect when additionally combined with a forward extraction temperature of 50-60° C. and a dissolved magnesium chloride concentration of at least 10 wt. %, based on the total amount of water and dissolved material present in the aqueous mixture. The organic liquid used is in this case preferably a ketone, more preferably MIBK. The back-extraction is in this case preferably conducted at 20-60° C., more preferably at 50-60° C. An even better concentration effect is obtained when using a magnesium chloride concentration of at least 15 wt. % instead of at least 10 wt. %, based on the total amount of water and dissolved material present in the aqueous mixture.

Thus, the following combination of parameters may result in particular good concentration effect and may at the same time result in a good extraction yield:
- a magnesium chloride concentration of at least 10 wt. %, based on the total amount of water and dissolved material present in the aqueous mixture;
- a forward extraction temperature of 30-60° C., in particular 50-60° C.;
- a back extraction temperature of 20-60° C.;
- a weight amount of organic liquid used in forward extraction that is 1.1/DR to 1.2/DR times the weight amount of aqueous mixture;
- a weight amount of aqueous liquid used in back extraction that is 1.1*DR to 1.2*DR times the weight amount of organic carboxylic acid solution;
- the organic liquid being a ketone, preferably MIBK.

The above combination works even better when using a magnesium chloride concentration of at least 15 wt. %, based on the total amount of water and dissolved material present in the aqueous mixture.

The total yield of the method of the invention depends both on the extraction yield in forward extraction and the extraction yield in back extraction.

The yield of forward extraction can be increased by conducting the forward extraction with counter-current streams (see also above). Such counter-current extraction can be conducted in one or more vessels (e.g. a mixer or settler). The yield of the extraction step can be increased by increasing the size and/or the number of the vessel(s). When using more than one vessel, the vessels are connected in series with each other. In this case, the second or further vessel further extracts the aqueous liquid obtained after extraction in the previous vessel. Preferably however, forward extraction is conducted in one vessel (e.g. an extraction column) that is sufficiently large to obtain the desired high yield (typically above 99%). For example, large extraction columns with a height of 10-20 meter are known in the art. The skilled person will be able to adjust the size and/or number of the vessels to obtain a yield of 99% or more.

The yield of back extraction can be increased in the same way as described above for forward extraction. In case more than one vessel is used, the second or further vessel further extracts the organic liquid obtained after extraction in the previous vessel.

If so desired, the method of the invention may further comprise the step of concentrating the product aqueous carboxylic acid solution by evaporation of water. The water evaporated in this step may be recycled by reusing it as the aqueous liquid in back extraction. It is possible for the product aqueous carboxylic acid solution to comprise a minor amount of organic solvent and residue from the extraction step, if present e.g. of the order of 0.1-3 wt. % based on the total amount of the aqueous carboxylic acid solution. Where an evaporation step is carried out, organic solvent is also typically evaporated in the concentration step, often enhanced by a stripping effect of water.

As indicated above, the second organic liquid obtained in the back extraction can be recycled by reusing it as the first organic liquid in the forward extraction.

In the process according to the invention, the aqueous waste liquid obtained in forward extraction which comprises magnesium chloride is subjected to a thermal decomposition step at temperatures of at least 300° C., thereby forming a magnesium oxide and HCl.

In a preferred embodiment of the invention, magnesium oxide and/or HCl are recycled ate least in part to other stages in a process for carboxylic acid preparation. More specifically, the magnesium oxide preferably is recycled at least in part to the fermentation step, in the form of MgO or after conversion into magnesium hydroxide, e.g., by contacting the magnesium oxide with water to obtain a magnesium hydroxide slurry.

The HCl from the thermal decomposition step preferably is recycled at least in part to the acidification step. In one embodiment HCl is dissolved in water during or after thermal decomposition, thereby obtaining a HCl solution. In another embodiment, the HCl derived from the thermal decomposition step is provided to the acidification step in gaseous form.

In a preferred embodiment of the present invention, the aqueous mixture comprising carboxylic acid and at least 5 wt. % dissolved magnesium chloride is derived from the steps of
  subjecting a carbon source to a fermentation step to form a carboxylic acid, which fermentation step comprises the steps of fermenting a carbon source by means of a micro-organism in a fermentation broth to form carboxylic acid and neutralizing at least part of the carboxylic acid by adding a magnesium base selected from magnesium oxide and magnesium hydroxide, thereby obtaining a magnesium carboxylate,
  subjecting the magnesium carboxylate to an acidification step wherein the magnesium carboxylate is contacted with HCl in an aqueous environment to form an aqueous mixture comprising carboxylic acid and magnesium chloride.

In the first step a carbon source is subjected to a fermentation step to form a carboxylic acid, which fermentation step comprises the steps of fermenting a carbon source by means of a micro-organism in a fermentation broth to form carboxylic acid and neutralizing at least part of the carboxylic acid by adding a magnesium base selected from magnesium oxide and magnesium hydroxide, thereby obtaining a magnesium carboxylate.

Fermentation processes for the manufacture of carboxylic acids are known in the art and require no further elucidation here. It is within the scope of the skilled person to select, using his common general knowledge, a suitable fermentation process, depending on the desired acid to be produced, the carbon source and the microorganism available.

The product of the fermentation process is a fermentation broth, which is an aqueous liquid comprising magnesium carboxylate, biomass, and optionally further components such as impurities like are sugars, proteins, and salts.

If so desired, the fermentation broth may be subjected to a biomass removal step, e.g., a filtration step, before further processing. This is generally preferred for improving product quality. Depending on the carboxylic acid produced, another intermediate step may be separation of solid reaction product, e.g., magnesium carboxylate, from the fermentation broth, before, after, or simultaneous with biomass removal, and optionally subjecting the magnesium carboxylate to a washing step.

Depending on the carboxylic acid produced, another intermediate step may be subjecting the fermentation broth to a concentration step to increase the concentration of magnesium carboxylate in the composition before acidification. This step may be carried out before, after, or simultaneous with biomass removal.

Other intermediate steps, e.g., purification steps, may be carried out as desired, as will be evident to the skilled person.

The next step in the process according to the invention is subjecting the magnesium carboxylate to an acidification step, also sometimes indicated as acidulation step, wherein the magnesium carboxylate is contacted with HCl in an aqueous environment to form an aqueous mixture comprising carboxylic acid and magnesium chloride.

There are various ways in which this step can be effected. The acidulation step is typically conducted by bringing the carboxylate salt in contact with an acidic HCl solution. However, in some embodiments it may also be possible to contact the carboxylate salt with gaseous HCl.

The carboxylate salt may be in solid and/or dissolved form. In one embodiment, the carboxylate salt is provided in solid form. In this case, the acidulation step is conducted by bringing the carboxylate salt in contact with an acidic solution. The advantage of preparing the aqueous mixture from carboxylate salt in solid form is that very high carboxylic acid concentration can thus be obtained, such as concentration of at least 15 wt. %, in particular at least 25%, up to, e.g. 50 wt. %, or e.g. 40 wt. %.

The carboxylate salt may also be in dissolved form, typically as part of an aqueous solution. In this case, the acidulation step can be conducted by bringing the carboxylate salt in contact with an acidic solution or an acidic gas.

The acidulation step may also be conducted on a mixture of carboxylic acid and carboxylate salt. Such a mixture may for example be obtained in a low pH fermentation. The mixture may for example be an aqueous suspension.

When acidulation of the carboxylate salt is conducted by contacting it with an acidic HCl solution, it preferably has an acid concentration as high as possible. Such a high acid concentration will result in an aqueous mixture with a high carboxylic acid concentration, which is desirable. The acidic solution therefore comprises at least 5 wt. %, more preferably at least 10 wt. % and even more preferably at least 20 wt. % acid, based on the total weight of the acidic solution. Acidulation is typically conducted using an excess of acid. The excess is preferably small, such that the aqueous mixture obtained is not highly acidic, which may not be desirable in view of further processing such a mixture. For example, the excess of acid used may be such that the resulting aqueous mixture has a pH 2 or lower, preferably a pH of 0-1.

In case gaseous HCl is used, it may be contacted by bringing it in contact with a carboxylate solution or suspension. In particular, HCl gas may be blown through the solution or suspension.

Preferably, acidulation is conducted at a temperature of 75° C. or less. At higher temperatures, it becomes uneconomical to adapt equipment to the harsh conditions of an acidic environment at high temperatures.

During acidulation, preferably no precipitation of carboxylic acid occurs. In one embodiment of the invention it is preferred for the carboxylic acid formed in the acidulation step to have a higher solubility than the salt formed in the acidulation step. This may prevent or at least decrease the chance of precipitation of the carboxylic acid during the acidulation step. In case precipitation would occur, the salt will precipitate first. For example, as $MgCl_2$ is formed in the acidulation step, the carboxylic acid preferably has a solubility in water that is higher than 60 g/100 g water at 20° C.

The HCl used in the acidification step of the process according to the invention preferably is at least partially derived from the thermal decomposition step described below. Preferably, at least 80% of the HCl is derived from the thermal decomposition step, more in particular at least 90%, more in particular at least 95%.

If so desired, after acidulation and before extraction, any solid material may be removed from the aqueous mixture, for example by filtration. The presence of solid material in the aqueous mixture in not desirable during extraction.

As has been described in more detail above, the extraction step is carried out on an aqueous medium comprising at least 5 wt. % of magnesium chloride. If the product obtained from the acidulation step does not meet this requirement, various measures may be taken. In one embodiment, magnesium chloride is added until the desired concentration is reached. In another embodiment, a concentration step is carried out to increase the concentration of magnesium chloride by removal of water. The aqueous mixture may be concentrated after acidulation prior to extraction to a concentration up to the solubility of the magnesium chloride and the carboxylic acid, in particular to a desirable concentration of dissolved magnesium chloride, as will be described in more detail below. During concentration, preferably no or substantially no precipitation of carboxylic acid or magnesium chloride should occur.

Thus, the integrated process according to the invention provides for a process wherein the waste material is recycled and wherein consequently relatively little waste is produced. Further, the product carboxylic acid solution has good properties, and the thermal decomposition step can be carried out in a HSE-acceptable manner without necessitating additional apparatus.

The method of the invention is preferably a continuous process. However, it may also be conducted as a batch process.

FIG. 1 illustrates a preferred embodiment of the present invention. The invention is not in any way limited to what is disclosed herein.

In FIG. 1, a fermentation process is carried out in fermentation reactor (1), comprises a carbon source and a microorganism. Feedstock and nutrients are provided to the reactor through lines not shown. In the fermentation reactor, a carboxylic acid is formed. To prevent a decrease in pH, magnesium hydroxide is added through line (19) as neutralising agent, to convert the carboxylic acid into magnesium carboxylate. Fermentation broth is withdrawn from the reactor through line (2), and provided to biomass separation unit (3), which is, e.g., a filtration unit. A fraction containing biomass is removed through line (4), and the resulting liquid comprising magnesium carboxylate is provided through line (5) to acidification unit (6), where it is subjected to an acidification step using HCl provided through line (17). Where the magnesium carboxylate is in an aqueous medium, as in the case provided here, the HCl may be in gaseous form or in the form of an aqueous solution, obtained by an absorption step in water (not shown). Where the magnesium carboxylate is in solid form, e.g. in the case of an intermediate evaporation step having been carried out, the HCl is generally provided in the form of an aqueous solution. The acidified liquid is an aqueous mixture comprising carboxylic acid and magnesium chloride. If so desired it may be subjected to a concentration step (not shown) to increase the concentration of magnesium chloride to the desired value. Provision of additional magnesium chloride is also possible.

An aqueous mixture comprising carboxylic acid and at least 5 wt. % dissolved magnesium chloride is provided through line (7) to an extraction reactor (8), where it is contacted with organic liquid provided through line (12). A stream (9), which comprises carboxylic acid in the organic liquid is withdrawn from the extraction reactor (8). Aqueous waste liquid (13) is also withdrawn from extraction reactor (8). Stream (9) comprising carboxylic acid in the organic liquid is provided to back-extraction reactor (10), where it is contacted with aqueous liquid provided through line. The product aqueous carboxylic acid solution is withdrawn through line (11). The organic liquid is withdrawn through line (12), and recycled to the extraction reactor (8), optionally after intermediate purification steps (not shown).

Aqueous waste liquid (13), which comprises magnesium chloride, is provided to a thermal decomposition unit (14), where it is subjected to a thermal decomposition step at a temperature of at least 300° C., thereby decomposing the magnesium chloride to magnesium oxide and HCl, with resulting water. The water is removed through line (20). The HCl is removed through line (17), and provided at least in part to acidification unit (6), either directly in gaseous form, or with an intermediate adsorption step in water to form an aqueous solution. The magnesium oxide is withdrawn through line (16) and recycled to fermentation reactor (1), in this case via hydration unit (18) where it is reacted with water to form magnesium hydroxide, which is provided to the fermentation reactor through line (19).

It is noted that the present specification describes a number of processing steps. It is the explicit intention that processing steps described herein may be combined as desired.

The present invention will be illustrated by the following examples, without being limited thereto or thereby.

EXAMPLE 1

Comparison of MIBK and Isoamyl Alcohol

This experiment was conducted to compare the stability of two solvents, MIBK and Isoamyl alcohol in contact with the 2-hydroxy butyric acid feed solution prepared by adding 340 g of crystalline hydroxy butyric acid to 720 g water and mixing to complete dissolution. The thus prepared feed solution comprised 32 wt % of hydroxy butyric acid.

For each solvent a closed glass reactor was filled with 20 g of solvent and 20 g of the hydroxy butyric acid feed solution, put in an oven to maintain a temperature of 60° C. and shaken continuously. After 3 hours, 24 hours (1 day) and 168 hours (1 week) the shaking was stopped for 1 hour to allow the phases to settle, a sample was taken from the solvent top layer, and the composition of the solvent top layer analyzed by gas chromatography. The results show that even after 168 hours no changes in the purity of the MIBK could be detected while in case of isoamyl alcohol 14.3 area % of isoamylhydroxybutyrate was formed after 3 hours. In the 24 hours and 168 hours samples the isoamylhydroxybutyrate concentration was found to have increased further to 21.5 area %.

This example shows that esters with the hydroxy butyric acid are formed when alcohols such as isoamyl alcohol are used as organic extraction solvent while ketones such as MIBK are stable organic solvents. It can be concluded that unstable organic solvents such as alcohols are unsuitable as extraction solvent and that stable organic solvents such as ketones are suitable extraction solvents. It should be noted in this respect that the esters formed will end up in the product carboxylic acid solution, and are difficult to remove therefrom.

EXAMPLE 2

Effects of Dissolved Salt Concentration and Temperature on Solvent Solubility 50 g organic solvent was added to 100 g of an aqueous solution with a specified MgCl2 concentration and the resulting two phase system stirred at a specified temperature for 30 minutes with sufficient speed to ensure that both phases are well dispersed. Hereafter, the stirring was stopped, the phases were allowed to separate and a sample was taken from the aqueous bottom phase. The concentration of solvent in this sample was determined by gas chromatography. The experiment was conducted for three different MgCl2 concentrations (0, 15 and 30 wt. %) and for MIBK also at two different temperatures (20° C. and 60° C.). The results are shown in Table 2.1 and 2.2.

TABLE 2.1

| $MgCl_2$ (wt %) | MIBK solubility (wt %) | |
|---|---|---|
| | 20° C. | 60° C. |
| 0 | 1.8 | 1.4 |
| 15 | 0.48 | 0.20 |
| 30 | 0.17 | 0.11 |

Table 2.1 shows that the addition of salt significantly reduces the solubility of the MIBK organic solvent in the aqueous phase. It can be concluded that the presence of salt significantly reduces the loss of organic solvent in the aqueous phase after extraction of the carboxylic acid.

TABLE 2.2

| | Solvent solubility (wt %) 20° C. | | |
|---|---|---|---|
| $MgCl_2$ (wt %) | MIBK | Isoamyl alcohol | Diisopropyl ether |
| 0 | 1.8 | 2.8 | 1.0 |
| 15 | 0.5 | 1.5 | 0.4 |
| 30 | 0.1 | 0.6 | 0.7 |

Table 2.2 shows that the solubility of isoamylalcohol in the magnesium chloride solution is significantly higher than that of MIBK, leading to more solvent loss. For diisopropylether at high salt concentrations the solubility of the solvent in the salt solution increases, resulting in high solvent loss. Thus, both for diisopropylether and for isoamylalcohol more solvent will remain in the salt solution that will be provided to the thermal decomposition unit than for MIBK.

EXAMPLE 3

Extraction of Different Types of Acids

The following general procedure was applied for glycolic acid, 3-hydroxy propionic acid, and 2-hydroxy butyric acid. A feed solution was prepared comprising acid and magnesium chloride. The solutions were stirred overnight.

1000 g of this feed solution was mixed with approximately 100 g of methyl-isobutylketone as solvent and stirred at 20° C. for minimum of 15 minutes. The mixture was transferred to a separation funnel where phases were separated. Samples of both phases were taken for analysis. Then approximately 100 g of organic phase was mixed with 10 g of pure water and stirred for minimum of 15 min at 20° C. Subsequently the whole mixture is again transferred to the separation funnel, phases are left to separate and samples of both phases are taken. Samples were analysed on acid content.

The results are presented in table 3.1

TABLE 3.1

| Example | Acid type | wt. % acid in feed | wt. % $MgCl_2$ in feed | wt. % acid in product |
|---|---|---|---|---|
| 3.1 | glycolic acid | 15 | 9 | 7.5 |
| | glycolic | 23 | 15 | 15 |
| 3.2 | 3-hydroxy propionic acid | 8 | 5 | 4 |
| | 3-hydroxy propionic acid | 27 | 15 | 21 |
| 3.3 | 2-hydroxy butyric acid | 13 | 7 | 15 |
| | 2-hydroxy butyric acid | 34 | 15 | 21 |

EXAMPLE 4

Removal of Solvent from Acid Product

A 2-hydroxy butyric acid feed solution (aqueous mixture) was prepared by adding magnesium chloride hexahydrate (790 g) to a solution of 700 g of crystalline lactic acid in 924 g water and mixing to complete dissolution. The thus prepared feed solution comprised 34 wt % of 2-hydroxy butyric acid and 15 wt % of magnesium chloride.

Two solvents, MIBK according to the invention and trioctylamine not according to the invention were applied in forward extraction, in accordance with the following procedure. In the forward extraction the feed solution described above was contacted with solvent at 20° C. in a solvent:feed weight-based ratio of 1:10. The resulting two phase system was stirred at 20° C. for 30 minutes with sufficient speed to ensure that both phases were well dispersed. Hereafter, the stirring was stopped, the phases were allowed to separate and the 2-hydroxy butyric acid loaded solvent layer was separated from the depleted aqueous 2-hydroxy butyric acid solution. In the back extraction this 2-hydroxy butyric acid loaded solvent layer was contacted at 20° C. with water in a solvent:water weight-based ratio of 1:10. The resulting two phase system was stirred at 20° C. for 30 minutes with sufficient speed to ensure that both phases are well dispersed. Hereafter, the stirring was stopped, the phases were allowed to separate and a sample was taken from the aqueous bottom phase.

As a final step the solvent residues were removed from the aqueous bottom phase by feeding to an atmospheric packed stripping column and evaporating 50% (weight basis) of the solvent loaded product in the form of steam. The residual solvent concentration in the aqueous product solution was determined by gas-chromatography. The results are summarized in table 4.1.

TABLE 4.1

| Solvent | 2-hydroxy butyric acid in aqueous product (wt. %) | Solvent residue before stripping (mg/kg) | Solvent residue after stripping (mg/kg) |
| --- | --- | --- | --- |
| MIBK | 22 | 24000 | 0.6 |
| Trioctylamine | 15 | 9 | 20 |

This example shows that MIBK can be easily removed to very low levels by stripping with in situ formed steam while amines are not removed from the product, but even concentrated due to their low volatility and entrainment in the steam.

EXAMPLE 5

Lactic Acid Extraction in the Presence of Dissolved Salt

A lactic acid feed solution (aqueous mixture) was prepared by adding magnesium chloride hexahydrate (790 g) to a solution of 700 g of crystalline lactic acid in 924 g water and mixing to complete dissolution. The thus prepared feed solution comprised 29 wt % of lactic acid and 15.3 wt % of magnesium chloride.

In the forward extraction an amount of 100 g MIBK was added to 1000 g of the lactic acid feed solution (weight-based ratio of 1:10). The resulting two phase system was stirred at 20° C. for 30 minutes with sufficient speed to ensure that both phases were well dispersed. Hereafter, the stirring was stopped, the phases were allowed to separate and the lactic acid loaded MIBK layer was separated from the depleted aqueous lactic acid solution. In the back extraction 4.7 g of water was added to 46.9 g of this lactic acid loaded MIBK layer (weight-based ratio of 1:10). The resulting two phase system was stirred at 20° C. for 30 minutes with sufficient speed to ensure that both phases are well dispersed. Hereafter, the stirring is stopped, the phases were allowed to separate and a sample was taken from the aqueous bottom phase. The concentration of lactic acid in this sample was 34.8 wt % (determined via potentiometric titration).

This example shows that the presence of dissolved magnesium chloride salt in the forward extraction increases the lactic acid concentration from 29 wt % in the feed solution to 34.8 wt % in the aqueous solution after back extraction.

In case the solution would be subjected to an evaporation step after extraction, the increased lactic acid concentration in the aqueous solution from the back extraction would thus reduce the amount of water that needs to be evaporated from the lactic acid product compared to the aqueous solution obtained after back extraction from the feed solution without dissolved magnesium chloride in example 1 by a factor 2.

EXAMPLE 6

Regular Temperature Swing Lactic Acid Extraction

In the forward extraction an amount of 100 g MIBK was added to 1000 g of the lactic acid feed solution (weight-based ratio of 1:10) as prepared in example 2 above. The resulting two phase system was stirred at 20° C. for 30 minutes with sufficient speed to ensure that both phases were well dispersed. Hereafter, the stirring was stopped, the phases were allowed to separate and the lactic acid loaded MIBK layer was separated from the depleted aqueous lactic acid solution. In the back extraction 6.9 g of water was added to 67.2 g of this lactic acid loaded MIBK layer (weight-based ratio of 1:10). The resulting two phase system was stirred at 60° C. for 30 minutes with sufficient speed to ensure that both phases are well dispersed. Hereafter, the stirring is stopped, the phases were allowed to separate and a sample was taken from the aqueous bottom phase. The concentration of lactic acid in this sample was 36.2 wt % (determined via potentiometric titration).

This example shows that applying a combination of dissolved magnesium chloride and a higher temperature in the back extraction yields an increased lactic acid concentration of 36.2 wt % in the aqueous solution after back extraction compared to the isothermal conditions applied in example 2. It can be concluded that applying an increased temperature in the back extraction is an efficient means of further concentrating the lactic acid during extraction.

EXAMPLE 7

Reverse Temperature Swing Lactic Acid Extraction

In the forward extraction an amount of 100 g MIBK was added to 997 g of the lactic acid feed solution (weight-based ratio of 1:10) as prepared in example 2. The resulting two phase system was stirred at 60° C. for 30 minutes with sufficient speed to ensure that both phases were well dispersed. Hereafter, the stirring was stopped, the phases were allowed to separate and the lactic acid loaded MIBK layer was separated from the depleted aqueous lactic acid solution. In the back extraction 5.8 g of water was added to 58 g of this lactic acid loaded MIBK layer (weight-based ratio of 1:10). The resulting two phase system was stirred at 20° C. for 30 minutes with sufficient speed to ensure that both phases were well dispersed. Hereafter, the stirring was stopped, the phases were allowed to separate and a sample was taken from the aqueous bottom phase. The concentration of lactic acid in this sample was 37.1 wt % (determined via potentiometric titration).

This example shows that applying a combination of dissolved magnesium chloride and a higher temperature in the forward extraction yields an increased lactic acid concentration of 37.1 wt % in the aqueous solution after back extraction compared to the isothermal conditions applied in example 2.

It can be concluded that applying an increased temperature in the forward extraction is an efficient means of further concentrating the lactic acid during extraction.

EXAMPLE 8

Increased Temperature Lactic Acid Extraction

In the forward extraction an amount of 100 g MIBK was added to 996 g of the lactic acid feed solution (weight-based ratio of 1:10) as prepared in example 2. The resulting two phase system was stirred at 60° C. for 30 minutes with sufficient speed to ensure that both phases were well dispersed. Hereafter, the stirring was stopped, the phases were allowed to separate and the lactic acid loaded MIBK layer was separated from the depleted aqueous lactic acid solution. In the back extraction 6.2 g of water was added to 63 g of this lactic acid loaded MIBK layer (weight-based ratio of 1:10). The resulting two phase system was stirred at 60° C. for 30 minutes with sufficient speed to ensure that both phases were well dispersed. Hereafter, the stirring was stopped, the phases were allowed to separate and a sample was taken from the aqueous bottom phase. The concentration of lactic acid in this sample was 36.0 wt % (determined via potentiometric titration).

This example shows that applying a combination of dissolved magnesium chloride and a higher temperature in the forward as well as back extraction yields an increased lactic acid concentration of 36.0 wt % in the aqueous solution after back extraction compared to the isothermal conditions applied in example 2. It can be concluded that isothermal operation at an increased temperature during forward and extraction is an efficient means of further concentrating the lactic acid during extraction.

EXAMPLE 9

Effect of Dissolved Salt Concentration and Temperature on Distribution Ratio 100 g MIBK organic solvent was added to 100 g of an aqueous solution with the desired MgCl2 and initial lactic acid concentration of 20 wt %. The resulting two phase system was stirred at 20° C. or 60° C. for 30 minutes with sufficient speed to ensure that both phases are well dispersed. Hereafter, the stirring is stopped, the phases were allowed to separate and samples were taken from both phases. The concentration of lactic acid (wt %) in these samples was determined by potentiometric titration. Hereafter the distribution ratio was calculated as the ratio of the lactic acid concentration (wt %) in the MIBK organic solvent phase divided by the lactic acid concentration (wt %) in the aqueous phase. The results are shown in Table 9.1.

TABLE 9.1

| | Lactic acid distribution ratio (wt %/wt %) | |
|---|---|---|
| $MgCl_2$ (wt %) | 20° C. | 60° C. |
| 0 | 0.16 | 0.19 |
| 10.5 | 0.33 | 0.37 |
| 16.0 | 0.49 | 0.56 |

This example shows that with increasing salt concentration the lactic acid distribution ratio increases significantly. Furthermore, the example also shows that the distribution ratio can be increased by raising the temperature. It can be concluded that the presence of salt and/or an increase in temperature significantly increase the extraction efficiency of carboxylic acids from the aqueous feed stream into the organic solvent.

EXAMPLE 10

Pilot Extraction Lactic Acid

The pilot extraction experiments were conducted in a Pulsed Disc and Donut Column (PDDC) pilot set-up containing an active column section of four thermo stated glass segments of each 1.04 m length and 40 mm internal diameter. This active section was enclosed on both sides by 42 cm long settlers, both having an inner diameter of 80 mm. The column internals consisted of alternately placed disc and doughnut baffles with a spacing of 8.4 mm made of PVDF to ensure wetting by the organic solvent phase. The bottom settler is connected to a piston type pulsator to pulse the liquid in the column at a desired frequency and amplitude. The aqueous solutions were introduced in the top and the MIBK organic solvent at the bottom of the column. The column was operated with the MIBK organic solvent as the continuous phase and the aqueous solutions as the dispersed phase. The interface level in the bottom settler was observed visually and controlled via a manually operated valve in the aqueous stream leaving the bottom of the column. The MIBK organic solvent was allowed to leave the column top settler via an overflow.

In the forward extraction the lactic acid feed solution (7 kg/hr), prepared in a similar way as in Example 5, was contacted counter currently in the PDDC pilot setup with MIBK (9.3 kg/hr) at a temperature of 60° C. The pulsator was operated with a frequency of 90 min-1 and amplitude of 11 mm. The lactic acid loaded MIBK organic solvent was collected during several hrs to collect a sufficient amount for the back extraction. In the back extraction the lactic acid loaded MIBK organic solvent (10.4 kg/hr) was counter currently contacted with water (2.5 kg/hr) in the PDDC setup at a temperature of 20° C. The pulsator was operated with a frequency of 67.5 min-1 and amplitude of 11 mm. Samples were taken from the aqueous bottom phase. The concentration of lactic acid in this sample was 34.5 wt % (determined via potentiometric titration).

This example shows that applying a dissolved magnesium chloride combined with a higher temperature in the forward extraction increases the lactic acid concentration from 29 wt % in the feed solution to 34.5 wt % in the aqueous solution after back extraction. It can be concluded that applying a dissolved magnesium chloride eventually combined with an increased temperature in the forward extraction in an extraction column is an efficient means of concentrating the lactic acid during extraction.

From the forward extraction a waste solution was withdrawn which contained 24 wt. % of magnesium chloride, 2.4 wt. % of lactic acid, and 0.16 wt, % of MIBK. This waste solution can be provided to a thermal decomposition step to be decomposed into magnesium oxide and hydrogen chloride.

EXAMPLE 11

Comparison of Different Solvents in Lactic Acid Extraction

Feed solutions were prepared comprising 29 wt % lactic acid and 15 wt. % magnesium chloride. The solutions were stirred overnight. Extraction took place as follows:

1000 g of a feed solution was mixed with approximately 100 g of solvent and stirred at 20° C. for minimum of 15 minutes. The mixture was transferred to a separation funnel where phases were separated. Samples of both phases were taken for analysis. Then approximately 100 g of organic phase was mixed with 10 g of pure water and stirred for minimum of 15 min at 20° C. Subsequently the whole mixture was again transferred to the separation funnel, phases were left to separate and samples of both phases are taken. Samples were analysed on acid content. The results are presented in Table 11.1.

TABLE 11.1

| | Solvent | [lactic acid] feed (wt. %) | [lactic acid] product (wt. %) |
|---|---|---|---|
| 1 inv | 2-pentanone | 29 | 30 |
| 2 inv | methylisobutyl ketone | 29 | 35 |
| 3 inv | cyclo-hexanone | 29 | 32 |
| 4 inv | 2-hexanone | 29 | 35 |
| 5 inv | acetophenone | 29 | 34 |
| 6 inv | 2-heptanone | 29 | 34 |
| 7 inv | 2-octanone | 29 | 30 |

The data in Table 11.1 show that for the C5+ ketones concentration occurred, with best results being obtained for methyl isobutyl ketone.

EXAMPLE 12

Extraction of Different Types Polycarboxylic Acids

Solutions containing magnesium chloride as salt and, respectively succinic acid, itaconic acid, and fumaric acid. The composition of the feed solutions is presented in table 12.1. The results are given in tables 1.2, 1.3, and 1.4. These tables also give the concentration ratio, which is the ratio between the acid concentration in the product and the acid concentration in the feed.

TABLE 12.1

| Example | Acid type | wt. % acid | wt. % MgCl$_2$ |
|---|---|---|---|
| 1.1 | succinic acid | 1.5 | 15 |
| 1.2 | itaconic acid | 1.5 | 15 |
| 1.3 | fumaric acis | 0.12 | 15 |

TABLE 12.2

| Succinic acid | |
|---|---|
| [acid] feed | 1.5 wt. % |
| [acid] aqueous fraction after back extraction | 3.1 wt. % |
| concentration ratio | 2.1 |
| $D_{FE}$ | 0.86 |
| $D_{BE}$ | 0.26 |
| $D_{FE}/D_{BE}$ | 3.3 |

TABLE 12.3

| Itaconic acid | |
|---|---|
| [acid] feed | 1.5 wt. % |
| [acid] aqueous fraction after back extraction | 2.8 wt. % |
| concentration ratio | 1.9 |
| $D_{FE}$ | 2.83 |
| $D_{BE}$ | 1.07 |
| $D_{FE}/D_{BE}$ | 2.64 |

TABLE 12.4

| Fumaric acid | |
|---|---|
| [acid] feed | 0.12 wt. % |
| [acid] aqueous fraction after back extraction | 0.21 wt. % |
| concentration ratio | 1.8 |
| $D_{FE}$ | 1.75 |
| $D_{BE}$ | 0.24 |
| $D_{FE}/D_{BE}$ | 7.29 |

The invention claimed is:

1. Method for the recovery of carboxylic acid, the method comprising the steps of:
   a) subjecting an aqueous mixture comprising carboxylic acid and at least 5 wt. % dissolved magnesium chloride, based on the total weight of water and dissolved material in the aqueous mixture to a forward extraction step, wherein the aqueous mixture subjected to the forward extraction step has a pH of 2 or lower, where the carboxylic acid is extracted from the aqueous mixture into a first organic liquid comprising at least 90% of an organic solvent, the organic solvent being selected from the group of C5-C8 ketones, to obtain an organic carboxylic acid solution and an aqueous waste liquid comprising magnesium chloride,
   b) subjecting the organic carboxylic acid solution to a back extraction step where the carboxylic acid is extracted from the organic carboxylic acid solution into an aqueous liquid to obtain an aqueous carboxylic acid solution and a second organic liquid; and
   c) subjecting the aqueous waste liquid comprising magnesium chloride obtained in the forward extraction to a thermal decomposition step at a temperature of at least 300° C. to decompose the magnesium chloride to magnesium oxide and HCl; wherein
   the carboxylic acid is at least one member selected from the group consisting of: glycolic acid; butyric acid; valeric acid; succinic acid; propionic acid; 3-hydroxypropionic acid; 2-hydroxybutyric acid; 3-hydroxybutyric acid; 4-hydroxybutyric acid; citric acid; fumaric acid; itaconic acid; adipic acid; acrylic acid; levulinic acid; maleic acid; 2,5-furandicarboxylic acid; mandelic acid; malic acid; and tartaric acid.

2. Method according to claim 1, wherein the aqueous mixture comprising carboxylic acid and the at least 5 wt. % dissolved magnesium chloride of step a) is obtained by:
  subjecting a carbon source to a fermentation step to form a carboxylic acid, which fermentation step comprises the steps of fermenting a carbon source by means of a micro-organism in a fermentation broth to form carboxylic acid and neutralizing at least part of the carboxylic acid by adding a magnesium base selected from magnesium oxide and magnesium hydroxide to obtain a magnesium carboxylate; and
  subjecting the magnesium carboxylate to an acidification step where the magnesium carboxylate is contacted with HCl in an aqueous environment to form an aqueous mixture comprising carboxylic acid and magnesium chloride.

3. Method according to claim 1, wherein the aqueous mixture subjected to the forward extraction step comprises at least 15 wt. % dissolved magnesium chloride, based on the total weight of water and dissolved material in the aqueous mixture.

4. Method according to claim 1, wherein said first organic liquid comprises at least 95 wt. % of said organic solvent.

5. Method according to claim 1, wherein the carboxylic acid is selected from the group consisting of: propionic acid; acrylic acid; butyric acid; and valeric acid.

6. Method according to claim 1, wherein said first organic liquid used in the extraction step a) comprises substantially no extractants, said extractants being compounds which form a complex with the carboxylic acid to be extracted.

7. Method according to claim 1, wherein the organic liquid is essentially free of amines, ethers, and alcohols, which means that these compounds, if present at all, are each present in an amount of less than 2 wt. % calculated on the weight of the organic liquid.

8. Method according to claim 1, wherein the aqueous mixture subjected to the forward extraction step has a pH of 0-1.

9. Method according to claim 1, wherein the aqueous mixture comprising carboxylic acid and magnesium chloride obtained from the acidification step is subjected to a concentration step comprising concentrating the aqueous mixture prior to extraction to a dissolved salt concentration of at least 5 wt. %, based on the total weight of water and dissolved material in the aqueous mixture.

10. Method according to claim 2, wherein at least part of the HCl from the thermal decomposition step c) is recycled to the acidification step after having been dissolved in water to obtain a HCl-containing solution.

11. Method according to claim 2, wherein the magnesium oxide formed in the thermal decomposition step c) is converted to magnesium hydroxide, which is added as magnesium base to the fermentation step.

12. Method according to claim 2, wherein at least part of the magnesium oxide formed in the thermal decomposition step c) is recycled to the fermentation step, in the form of MgO or after conversion into magnesium hydroxide.

13. Method according to claim 2, wherein at least part of the HCl from the thermal decomposition step c) is recycled to the acidification step.

14. Method according to claim 1, wherein the carboxylic acid is at least one member selected from the group consisting of: succinic acid; propionic acid; 3-hydroxypropionic acid; citric acid; fumaric acid; itaconic acid; adipic acid; acrylic acid; levulinic acid; maleic acid; 2,5-furandicarboxylic acid; mandelic acid; malic acid; tartaric acid; 2-hydroxybutyric acid; 3-hydroxybutyric acid; and 4-hydroxybutyric acid.

15. Method according to claim 1, wherein the carboxylic acid is at least one member selected from the group consisting of: succinic acid; propionic acid; 3-hydroxypropionic acid; citric acid; 2-hydroxybutyric acid; 3-hydroxybutyric acid; and 4-hydroxybutyric acid.

16. Method according to claim 1, wherein said first organic liquid used in the extraction step a) comprises substantially no amine extractants, said amine extractants being amine compounds which form a complex with the carboxylic acid to be extracted.

17. Method according to claim 1, wherein said first organic liquid comprises at least 99 wt. % of said organic solvent.

18. Method according to claim 1, wherein the aqueous mixture subjected to the forward extraction step comprises at least 20 wt. % dissolved magnesium chloride, based on the total weight of water and dissolved material in the aqueous mixture.

19. Method according to claim 1, wherein the aqueous mixture subjected to the forward extraction step comprises at least 25 wt. % dissolved magnesium chloride, based on the total weight of water and dissolved material in the aqueous mixture.

20. Method according to claim 13, wherein said HCl is recycled to the acidification step in gaseous form.

21. Method according to claim 2, wherein said acidification step is conducted on a mixture of carboxylic acid and magnesium carboxylate.

22. Method for the recovery of carboxylic acid, said method comprising the steps of:
  a) subjecting an aqueous mixture comprising carboxylic acid and at least 5 wt. % dissolved magnesium chloride, based on the total weight of water and dissolved material in the aqueous mixture to a forward extraction step where the carboxylic acid is extracted from the aqueous mixture into a first organic liquid comprising at least 90 wt. % of an organic solvent, the organic solvent being selected from the group of C5-8 ketones, thereby obtaining an organic carboxylic acid solution and an aqueous waste liquid comprising magnesium chloride;
  b) subjecting the organic carboxylic acid solution to a back extraction step where the carboxylic acid is extracted from the organic carboxylic acid solution into an aqueous liquid to obtain a second organic liquid and an aqueous carboxylic acid solution whose concentration of carboxylic acids is higher than that of the aqueous mixture comprising carboxylic acid; and
  c) subjecting the aqueous waste liquid comprising magnesium chloride obtained in the forward extraction to a thermal decomposition step at a temperature of at least 300° C. to decompose the magnesium chloride to magnesium oxide and HCl,
  wherein the first organic liquid used in the extraction step a) comprises substantially no amine extractants, said amine extractants being amine compounds which form a complex with the carboxylic acid to be extracted.

23. Method for the recovery of carboxylic acid, said method comprising the steps of:
  a) subjecting an aqueous mixture comprising carboxylic acid and at least 5 wt. % dissolved magnesium chloride, based on the total weight of water and dissolved material in the aqueous mixture to a forward extraction step where the carboxylic acid is extracted from the aqueous mixture into a first organic liquid comprising at least 90 wt. % of an organic solvent, the organic solvent being selected from the group of C5-8 ketones, thereby obtaining an organic carboxylic acid solution and an aqueous waste liquid comprising magnesium chloride;

b) subjecting the organic carboxylic acid solution to a back extraction step where the carboxylic acid is extracted from the organic carboxylic acid solution into an aqueous liquid to obtain a second organic liquid and an aqueous carboxylic acid solution whose concentration of carboxylic acids is higher than that of the aqueous mixture comprising carboxylic acid; and c) subjecting the aqueous waste liquid comprising magnesium chloride obtained in the forward extraction to a thermal decomposition step at a temperature of at least 300° C. to decompose the magnesium chloride to magnesium oxide and HCl, wherein the first organic liquid used in the extraction step a) is essentially free of amines, ethers, and alcohols, which means that these compounds, if present at all, are each present in an amount of less than 2 wt. %, calculated on the weight of the first organic liquid.

24. The method according to claim 22, wherein the carboxylic acid is at least one member selected from the group consisting of: glycolic acid; butyric acid; valeric acid; succinic acid; propionic acid; 3-hydroxypropionic acid; 2-hydroxybutyric acid; 3-hydroxybutyric acid; 4-hydroxybutyric acid; citric acid; fumaric acid; itaconic acid; adipic acid; acrylic acid; levulinic acid; maleic acid; 2,5-furandicarboxylic acid; mandelic acid; malic acid; and tartaric acid.

25. The method according to claim 23, wherein the carboxylic acid is at least one member selected from the group consisting of: glycolic acid; butyric acid; valeric acid; succinic acid; propionic acid; 3-hydroxypropionic acid; 2-hydroxybutyric acid; 3-hydroxybutyric acid; 4-hydroxybutyric acid; citric acid; fumaric acid; itaconic acid; adipic acid; acrylic acid; levulinic acid; maleic acid; 2,5-furandicarboxylic acid; mandelic acid; malic acid; and tartaric acid.

* * * * *